(12) United States Patent
Park et al.

(10) Patent No.: US 12,161,439 B2
(45) Date of Patent: Dec. 10, 2024

(54) METHOD FOR PERFORMING WIRELESS COMMUNICATION BY USING BIOSENSOR AND ELECTRONIC DEVICE THEREFOR

(71) Applicant: Samsung Electronics Co., Ltd., Suwon-si (KR)

(72) Inventors: Chungsoon Park, Suwon-si (KR); Kyungmin Kim, Suwon-si (KR); Sujin Park, Suwon-si (KR); Hyunggon Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1020 days.

(21) Appl. No.: 17/043,388

(22) PCT Filed: Apr. 5, 2019

(86) PCT No.: PCT/KR2019/004047
§ 371 (c)(1),
(2) Date: Sep. 29, 2020

(87) PCT Pub. No.: WO2019/194626
PCT Pub. Date: Oct. 10, 2019

(65) Prior Publication Data
US 2021/0093198 A1 Apr. 1, 2021

(30) Foreign Application Priority Data
Apr. 5, 2018 (KR) .................. 10-2018-0039738

(51) Int. Cl.
*A61B 5/00* (2006.01)
*H02J 7/00* (2006.01)
(Continued)

(52) U.S. Cl.
CPC .......... *A61B 5/0017* (2013.01); *A61B 5/0059* (2013.01); *H02J 7/00045* (2020.01);
(Continued)

(58) Field of Classification Search
None
See application file for complete search history.

(56) References Cited

U.S. PATENT DOCUMENTS 8,204,587 B2 6/2012 Pak et al.
10,080,527 B2 9/2018 Golda et al.
(Continued)

FOREIGN PATENT DOCUMENTS

JP 2005-101853 A 4/2005
JP 2010-510023 A 4/2010
(Continued)

OTHER PUBLICATIONS

International Search Report and Written Opinion of the International Searching Authority in connection with International Application No. PCT/KR2019/004047 dated Jul. 30, 2019, 16 pages.
(Continued)

*Primary Examiner* — Patricia J Park

(57) ABSTRACT

Disclosed is an electronic device comprising: a biometric sensor, including at least one light emitting diode (LED) and at least one light receiving unit, for acquiring biometric information by means of the at least one light emitting device and the at least one light receiving unit; a power receiving circuit configured to receive a wireless power signal from an external electronic device; and a processor operatively coupled to the biometric sensor and the power receiving circuit. The processor may be configured to receive a designated wireless power signal from the external electronic device by using the power receiving circuit and to perform optical communication with the external electronic device by using the biosensor when the designated wireless power signal is received. Other various embodiments identified from the specification are also possible.

12 Claims, 11 Drawing Sheets

(51) Int. Cl.
    *H02J 7/04*        (2006.01)
    *H02J 50/12*      (2016.01)
    *H02J 50/20*      (2016.01)
    *H02J 50/80*      (2016.01)
    *H04B 10/50*     (2013.01)
    *H04B 10/69*     (2013.01)

(52) U.S. Cl.
    CPC .............. *H02J 7/0047* (2013.01); *H02J 7/04* (2013.01); *H02J 50/12* (2016.02); *H02J 50/20* (2016.02); *H02J 50/80* (2016.02); *H04B 10/502* (2013.01); *H04B 10/69* (2013.01); *A61B 2562/0233* (2013.01)

(56) References Cited

U.S. PATENT DOCUMENTS

| | | |
|---|---|---|
| 10,244,949 B2 | 4/2019 | Moyer et al. |
| 2006/0287589 A1 | 12/2006 | Wobermin et al. |
| 2010/0241057 A1 | 9/2010 | Pak et al. |
| 2013/0297844 A1 | 11/2013 | Rosenberg et al. |
| 2014/0059263 A1 | 2/2014 | Rosenberg et al. |
| 2014/0086592 A1 | 3/2014 | Nakahara et al. |
| 2014/0275871 A1* | 9/2014 | Lamego ............... A61B 5/0022 600/323 |
| 2015/0244201 A1* | 8/2015 | Chu .................... H02J 50/80 320/108 |
| 2016/0058375 A1 | 3/2016 | Rothkopf |
| 2016/0166153 A1* | 6/2016 | Woo ................... A61B 5/14552 600/324 |
| 2016/0261151 A1* | 9/2016 | Kim ...................... H02J 50/80 |
| 2016/0349795 A1 | 12/2016 | Rosenberg et al. |
| 2016/0378069 A1 | 12/2016 | Rothkopf |
| 2016/0378070 A1 | 12/2016 | Rothkopf |
| 2016/0378071 A1 | 12/2016 | Rothkopf |
| 2018/0165566 A1 | 6/2018 | Rogers et al. |
| 2018/0177459 A1 | 6/2018 | Eletr et al. |
| 2018/0210491 A1 | 7/2018 | Song et al. |
| 2018/0274973 A1 | 9/2018 | Rogers et al. |
| 2019/0029599 A1 | 1/2019 | Golda et al. |
| 2020/0233380 A1 | 7/2020 | Rothkopf et al. |

FOREIGN PATENT DOCUMENTS

| | | |
|---|---|---|
| JP | 2017-510390 A | 4/2017 |
| KR | 10-2005-0076408 A | 7/2005 |
| KR | 10-2017-0014847 A | 2/2017 |
| KR | 10-2018-0033468 A | 4/2018 |

OTHER PUBLICATIONS

Extended European Search Report issued May 26, 2021, in connection with European Patent Application No. 19781052.6, 8 pages.
Communication pursuant to Article 94(3) EPC dated Sep. 26, 2023, in connection with European Application No. 19781052.6, 5 pages.
Non-final Office Action dated Aug. 19, 2024, in connection with U.S. Appl. No. 18/650,981, 26 pages.

* cited by examiner

METHOD FOR PERFORMING WIRELESS COMMUNICATION BY USING BIOSENSOR AND ELECTRONIC DEVICE THEREFOR

CROSS-REFERENCE TO RELATED APPLICATIONS

This application is a 371 National Stage of International Application No. PCT/KR2019/004047, filed Apr. 5, 2019, which claims priority to Korean Patent Application No. 10-2018-0039738, filed Apr. 5, 2018, the disclosures of which are herein incorporated by reference in their entirety.

BACKGROUND

1. Field

Embodiments disclosed in the disclosure relate to a wireless communication method using a biometric sensor and an electronic device therefor.

2. Description of Related Art

As various portable electronic devices such as a smartphone are distributed, methods for detecting biometric information using a portable electronic device are being studied. A health care service for a user may be provided by sensing the biometric information using the portable electronic device. For example, an electronic device may include a biometric sensor capable of performing optical measurements. The biometric information such as a heart rate may be measured using a biometric sensor. For example, the electronic device may be a wearable device.

SUMMARY

An electronic device may support wireless charging. For example, when the electronic device is located within a specific distance from a power transmitting device such as a wireless charging pad, the electronic device may charge the battery of the electronic device, using an electromagnetic induction or resonance phenomenon between a transmission coil of a power transmitting device and a reception coil of the electronic device.

The electronic device or power transmission device (e.g., a wireless charger) may control wireless charging using in-band communication. Because the reception coil for power reception is used in the in-band communication, the type and the amount of information of a power signal capable of being identified and/or received by the electronic device may be restricted. Also, the power signal may be susceptible to noise from surrounding environments.

According to various embodiments disclosed in the specification, the electronic device may provide wireless communication with the power transmission device using a biometric sensor.

According to an embodiment disclosed in this specification, an electronic device may include a biometric sensor including at least one light emitting diode (LED) and at least one light receiving unit and obtaining biometric information using the at least one LED and the at least one light receiving unit, a power receiving circuit receiving a wireless power signal from an external electronic device, and a processor operatively coupled to the biometric sensor and the power receiving circuit. The processor may be configured to receive a specified wireless power signal from the external electronic device, using the power receiving circuit and to perform optical communication with the external electronic device, using the biometric sensor when receiving the specified wireless power signal.

Furthermore, according to an embodiment disclosed in this specification, an electronic device may include a light emitting unit outputting light, at least one light receiving unit, a power receiving circuit, and a processor. The processor may be configured to receive a request for obtaining a biometric signal corresponding to a living body, when receiving the request, to obtain at least part of light reflected by the living body among the light output through the light emitting unit, using the light receiving unit and then detect the biometric signal based at least partly on the obtained light, and when being coupled to an external electronic device using the power receiving circuit, to communicate with the external electronic device, using the light receiving unit and the light emitting unit.

Moreover, according to an embodiment disclosed in this specification, an optical communication method of an electronic device may include receiving a specified wireless power signal from the external electronic device, using a power receiving circuit of the electronic device, and performing optical communication with the external electronic device, using a biometric sensor of the electronic device when the specified wireless power signal is received. The biometric sensor may include at least one LED and at least one light receiving unit.

According to various embodiments disclosed in the specification, an electronic device may perform more robust communication by performing wireless communication using a biometric sensor.

According to various embodiments disclosed in the specification, an electronic device may perform faster and more reliable communication than communication with a power signal-based wireless charger.

According to various embodiments disclosed in the specification, various pieces of information may be provided to users through the communication between the electronic device and the wireless charger.

Besides, a variety of effects directly or indirectly understood through the disclosure may be provided.

With regard to description of drawings, the same or similar components will be marked by the same or similar reference signs.

DETAILED DESCRIPTION

Hereinafter, various embodiments of this specification may be described with reference to accompanying drawings. Embodiments and terms used herein are not intended to limit the technologies described in the disclosure to specific embodiments, and it should be understood that the embodiments and the terms include modification, equivalent, and/or alternative on the corresponding embodiments described herein.

Figure 1:
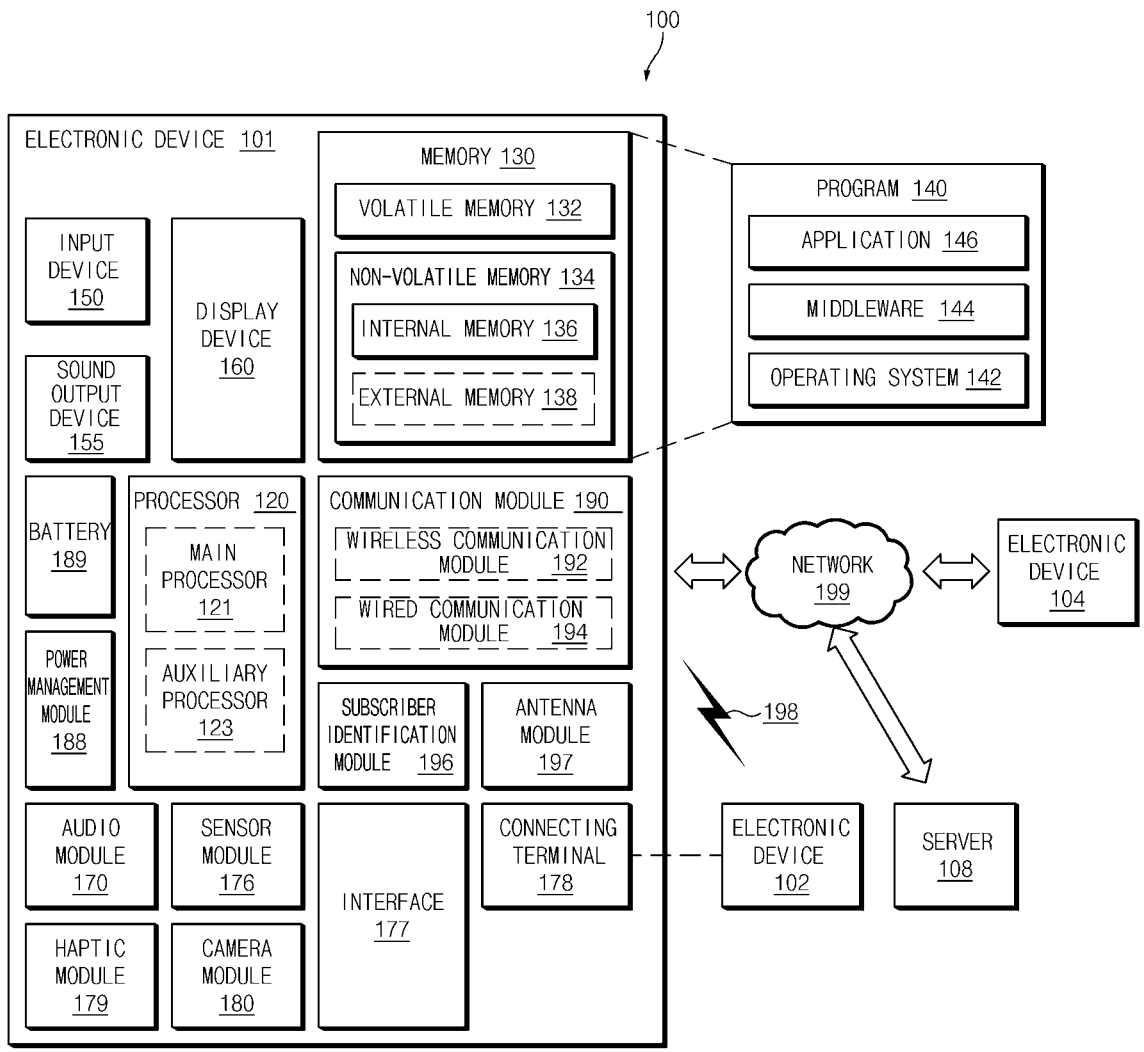
FIG. 1 is a block diagram of an electronic device in a network for performing wireless communication using a biometric sensor, according to various embodiments.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

Figure 2:
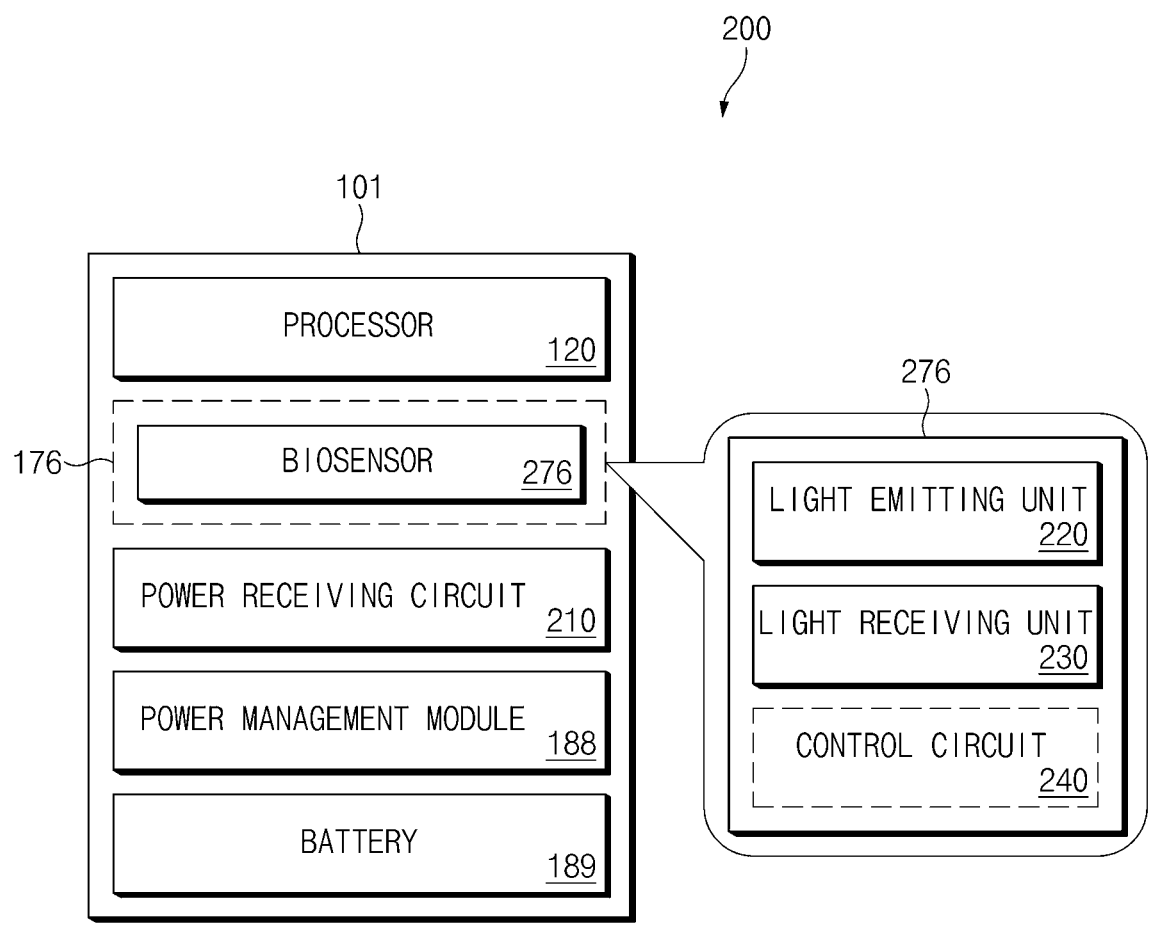
FIG. 2 illustrates a block diagram of an electronic device, according to various embodiments.

FIG. 2 illustrates a block diagram 200 of the electronic device 101 according to various embodiments.

According to various embodiments, the electronic device 101 may include the processor 120, the sensor module 176, the power management module 188, the battery 189, and a power receiving circuit 210. According to an embodiment, the electronic device 101 may further include other components not illustrated in FIG. 2. For example, the electronic device 101 may further include a memory (e.g., the memory 130 in FIG. 1), a device for receiving and outputting voice (e.g., the audio module 170 in FIG. 1), and/or a display (e.g., the display device 160 of FIG. 1).

According to various embodiments, the processor 120 may be electrically or operatively connected to other components of the electronic device 101 (e.g., the sensor module 176, the power management module 188, the battery 189, and/or the power receiving circuit 210) and may be configured to control other components of the electronic device 101. In the following embodiments, the operation of the electronic device 101 may be referred to as the operation of the processor 120. According to an embodiment, the processor 120 may perform the operations described later based on instructions stored in the memory 160.

According to various embodiments, the electronic device 101 may include at least one sensor configured to sense biometric information. For example, the electronic device 101 may detect biometric information (e.g., heart rate, oxygen saturation, blood pressure, and/or blood glucose) associated with an external object (e.g., a user or the like), using at least one biometric sensor 276 included in the sensor module 176. For example, the biometric sensor 276 may include a heart rate monitor (HRM) sensor for detecting heart rate information.

According to various embodiments, the biometric sensor 276 may include a light emitting unit 220, a light receiving unit 230, and a control circuit 240. According to an embodiment, the control circuit 240 may be implemented outside the biometric sensor 276. For example, the control circuit 240 may be omitted. According to an embodiment, the biometric sensor 276 may irradiate light of a specified wavelength, using the light emitting unit 220 and may obtain biometric information by sensing light reflected by an external object, using the light receiving unit 230. According to an embodiment, the biometric sensor 276 may obtain various pieces of biometric information (heart rate, oxygen saturation, blood pressure, and/or blood glucose) by irradiating light of various wavelengths.

According to various embodiments, when a request to obtain biometric information is received, the processor 120 may obtain the biometric information, using the biometric sensor 276. According to an embodiment, the processor 120 may output light using the light emitting unit 220, and may receive at least part of light obtained as the output light is reflected by an external object (e.g., a body), using the light receiving unit 230. The processor 120 may be configured to obtain the biometric information based on at least part of the received light. According to an embodiment, the processor 120 may adjust the wavelength and/or strength of the light output using the light emitting unit 220, based at least on the magnitude of the light received using the light receiving unit 230. For example, for calibration according to external environments (e.g., skin colors), the processor 120 may control the light emitting unit 220.

According to various embodiments, the light emitting unit 220 may include at least one light emitting element (e.g., a light emitting diode (LED)) for emitting light of a wavelength of a specified range. According to an embodiment, the light emitting unit 220 may include at least one light emitting element for emitting light having a wavelength (e.g., about 400 nm~about 1000 μm) of a specified range. According to an embodiment, the light emitting unit 220 may include a plurality of light emitting elements for emitting light corresponding to a plurality of wavelengths. For example, the light emitting unit 220 may include a plurality of LEDs corresponding to red (about 622 nm~780 nm), green (about 492 nm~577 nm), blue (about 492 nm~455 nm), and infrared (about 780 nm~1500 μm), respectively.

According to various embodiments, the light receiving unit 230 may include at least one light receiving unit (e.g., a photodiode) for detecting light. According to an embodiment, the light receiving unit 230 may be configured to detect light obtained as the light emitted by the light emitting unit 220 is reflected by an external object (e.g., a user). According to an embodiment, the light receiving unit 230 may detect light in a specified range and may output a current having a magnitude corresponding to the detected strength of light. According to an embodiment, the light receiving unit 230 may include at least one photo diode for detecting light having a wavelength (e.g., about 400 nm~about 1000 μm) of a specified range. For example, the light receiving unit 230 may include a plurality of filters for separating light of multiple wavelengths. According to an embodiment, the light receiving unit 230 may include a plurality of light receiving units for detecting light corresponding to a plurality of wavelengths. For example, the light receiving unit 230 may include a plurality of photodiodes capable of receiving light corresponding to red, green, blue, and infrared, respectively.

According to various embodiments, the control circuit 240 may control the light emitting unit 220 and the light receiving unit 230. For example, the control circuit 240 may control the light emitting unit 220 and/or the light receiving unit 230, under the control of the processor 120. According to an embodiment, the control circuit 240 may drive at least one LED of the light emitting unit 220. According to an embodiment, the control circuit 240 may process a signal detected by the light receiving unit 230. For example, the control circuit 240 may convert the current signal detected by the light receiving unit 230 to a voltage signal, may process (e.g., amplify and/or filter) the voltage signal, and may convert the processed voltage signal to a digital signal. According to an embodiment, the control circuit 240 may include a memory for storing biometric information detected by the light receiving unit 230 and/or instructions for controlling the light receiving unit 230 and the light emitting unit 220. According to an embodiment, the processor 120 may perform post-processing (e.g., filtering and/or noise cancelling) on the biometric information detected by the biometric sensor 276.

According to various embodiments, the electronic device 101 may be configured to charge the battery 189 based on a wireless power signal from an external electronic device. According to an embodiment, the electronic device 101 may receive a wireless power signal from an external electronic device (e.g., a wireless charger), using the power receiving circuit 210. For example, the power receiving circuit 210 may include a coil for receiving a wireless power signal. According to an embodiment, the power management module 188 may charge the battery 189 with the power received using the power receiving circuit 210. According to an embodiment, the power management module 188 may supply power to other configurations of the electronic device 101 with the power received using the power receiving circuit 210. According to an embodiment, the power management module 188 may manage the power supply under the control of the processor 120.

According to various embodiments, the electronic device 101 may detect the coupling with an external electronic device (e.g., a wireless charger), using the power receiving circuit 210. For example, when a specified wireless power signal (e.g., a wireless power signal having a specified magnitude and/or a specified time length) is received from an external electronic device, the electronic device 101 may identify the coupling with the external electronic device.

According to various embodiments, the electronic device 101 may communicate with an external electronic device (e.g., a wireless charger), using the power receiving circuit 210. In the following embodiments, a signal in the same band as a signal used for wireless charging based on electromagnetic induction and/or resonance may be referred to as a wireless power signal. According to an embodiment, the electronic device 101 may communicate with an external electronic device by receiving a signal of a specified radio frequency from the external electronic device, using the power receiving circuit 210. According to an embodiment, the electronic device 101 may communicate with an external electronic device by receiving a signal of a specified radio frequency, using a coil connected to the power receiving circuit 210 or the communication module 190. In the following embodiments, the electronic device 101 may perform optical communication using the biometric sensor 276.

Figure 3:
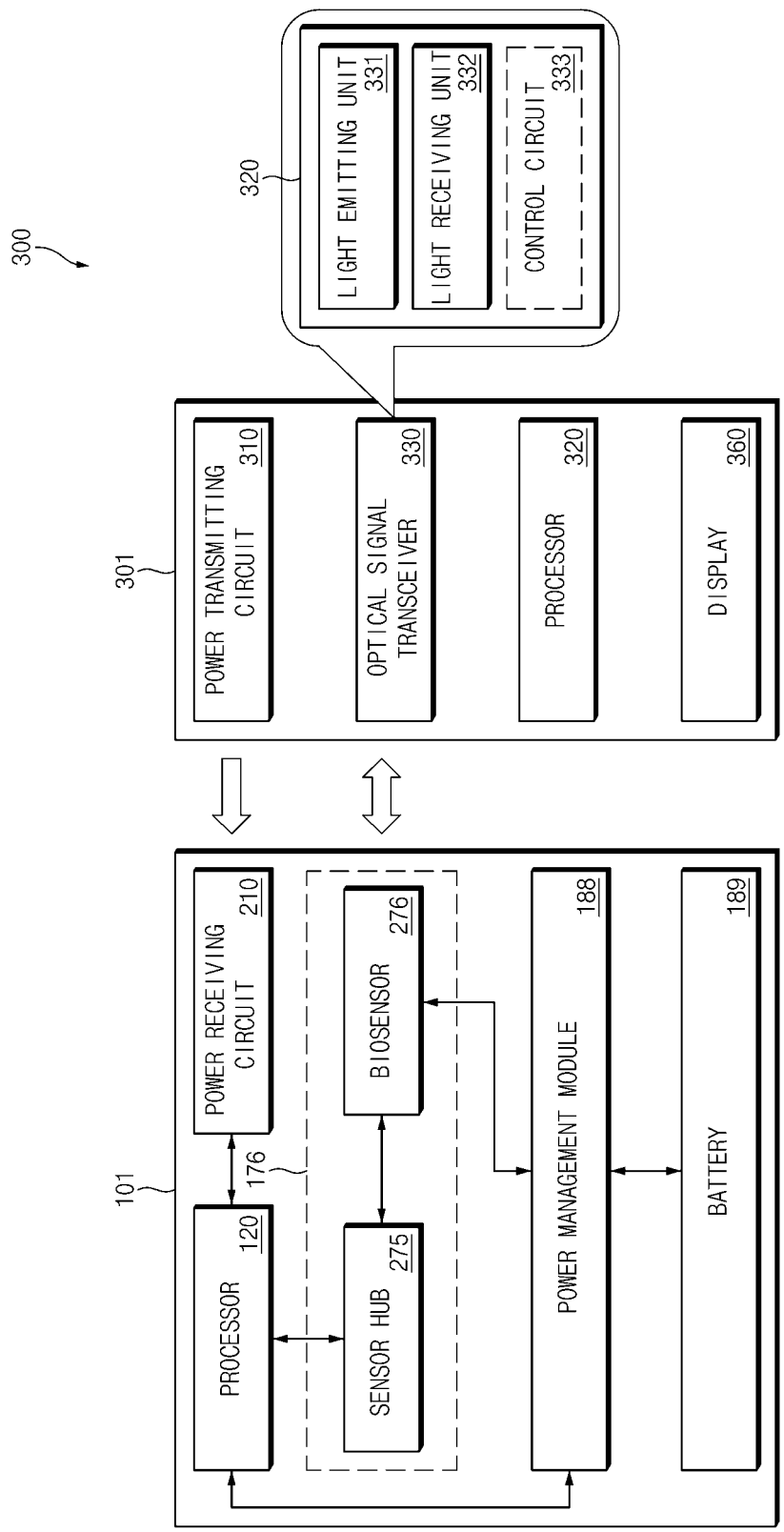
FIG. 3 is a block diagram of an electronic device and a wireless charger in a communication environment according to various embodiments.

FIG. 3 is a block diagram of the electronic device 101 and a wireless charger 301 in a communication environment 300 according to various embodiments.

A block diagram of the electronic device 101 illustrated in FIG. 3 is a diagram for describing a connection relationship between configurations of the electronic device 101 according to various embodiments. The configuration of the electronic device 101 is not limited thereto. The descriptions about a configuration having the same reference numeral may be referenced by the description associated with FIG. 2.

According to various embodiments, the sensor module 176 may include a sensor hub 275 and the biometric sensor 276. According to an embodiment, the sensor hub 275 may be coupled to the biometric sensor 276 through an inter-integrated chip (I2C) bus. According to an embodiment, the sensor hub 275 may operate between the processor 120 and at least one sensor including the biometric sensor 276. According to an embodiment, the sensor hub 276 may be included in the processor 120.

According to various embodiments, the wireless charger 301 may include a power transmitting circuit 310, a processor 320, an optical signal transceiver 330, and a display 360. The configuration of the wireless charger 301 shown in FIG. 3 is exemplary, and the configuration of the wireless charger 301 is not limited thereto. According to an embodiment, the wireless charger 301 may further include a configuration not illustrated in FIG. 3. For example, the wireless charger 301 may further include a connector (not illustrated) for receiving power from an external power source. According to an embodiment, the wireless charger 301 may not include at least one of components illustrated in FIG. 3. For example, the wireless charger 301 may not include the display 360. In the following embodiments, the wireless charger 301 may be referred to as an external electronic device.

According to various embodiments, the processor 320 may be electrically or operatively connected to other components of the wireless charger 301 (e.g., the power transmitting circuit 310, the optical signal transceiver 330, and/or the display 360) and may be configured to control other components of wireless charger 301. In the following embodiments, the operation of the wireless charger 301 may be referred to as the operation of the processor 320. According to an embodiment, the processor 320 may perform the operations described later based on instructions stored in the memory (not illustrated).

According to various embodiments, the power transmitting circuit 320 may be configured to transmit a wireless power signal. According to an embodiment, the power transmitting circuit 320 may generate a wireless power signal through the power transmitting circuit 320 under the control of the processor 320. For example, the power transmitting circuit 320 may include a coil for transmitting a wireless power signal based on electromagnetic induction and/or electromagnetic resonance. According to an embodiment, the power transmitting circuit 320 may be configured to transmit a signal of a specified radio frequency. For example, the power transmitting circuit 320 may transmit a signal of a specified radio frequency, using a coil for transmitting a wireless power signal.

According to various embodiments, the optical signal transceiver 330 may be configured to perform optical communication with the electronic device 101. According to an embodiment, the optical signal transceiver 330 may include a light emitting unit 331, a light receiving unit 332, and a control circuit 333. According to an embodiment, the control circuit 333 may be implemented to be placed outside of the optical signal transceiver 330. For example, the control circuit 333 may be omitted. According to an embodiment, the optical signal transceiver 330 may not include the light emitting unit 331. For example, the optical signal transceiver 330 may include only a light receiving unit for receiving light from the electronic device 101. In this case, the optical signal transceiver 330 may be referred to as an optical signal receiver.

According to various embodiments, the light emitting unit 331 may include at least one light emitting element (e.g., LED) for emitting light of a wavelength of a specified range. According to an embodiment, the light emitting unit 331 may include at least one light emitting element for emitting light having a wavelength (e.g., about 400 nm~about 1500 μm) of a specified range. According to an embodiment, the light emitting unit 220 may include a plurality of light emitting elements for emitting light corresponding to a plurality of wavelengths. For example, the light emitting unit 220 may include a plurality of LEDs corresponding to a red band (about 622 nm~780 nm), a green band (about 492 nm~577 nm), a blue band (about 492 nm~455 nm), and an infrared band (about 780 nm~1500 μm), respectively.

According to various embodiments, the light receiving unit 332 may include at least one light receiving unit (e.g., a photodiode) for detecting light. According to an embodiment, the light receiving unit 332 may be configured to detect the light emitted by the biometric sensor 276 of the electronic device 101. According to an embodiment, the light receiving unit 332 may detect light in a specified range and may output a current having a magnitude corresponding to the strength of the detected light. According to an embodiment, the light receiving unit 332 may include at least one photo diode for detecting light having a wavelength (e.g., about 400 nm~about 1500 μm) of a specified range. For example, the light receiving unit 332 may include a plurality of filters for separating light of multiple wavelengths. According to an embodiment, the light receiving unit 332 may include a plurality of light receiving units for detecting light corresponding to a plurality of wavelengths. For example, the light receiving unit 332 may include a plurality of photodiodes capable of receiving light corresponding to red, green, blue, and infrared, respectively.

According to various embodiments, the control circuit 333 may control the light emitting unit 331 and the light receiving unit 332. For example, the control circuit 333 may control the light emitting unit 331 and/or the light receiving unit 332, under the control of the processor 320. According to an embodiment, the control circuit 333 may drive at least one LED of the light emitting unit 331. According to an embodiment, the control circuit 333 may process a signal detected by the light receiving unit 332. For example, the control circuit 333 may convert the current signal detected by the light receiving unit 332 to a voltage signal, may process (e.g., amplify and/or filter) the voltage signal, and may convert the processed voltage signal to a digital signal.

According to various embodiments, the display 360 may be configured to display various pieces of information under the control of the processor 320. For example, the display 360 may include at least one LED. For example, the display 360 may include at least one of a liquid crystal display (LCD), an organic LED (OLED) display, and an LED display. According to an embodiment, the display 360 may be configured to display information received through the optical signal transceiver 330. For example, the display 360 may be configured to display information (e.g., at least one of identification information (e.g., model name) of the electronic device 101, a status of fast charging, a level of a status of charging level, or notifications of the electronic device 101) associated with the state of the electronic device 101.

According to various embodiments, the electronic device 101 may control the operating mode of the biometric sensor 276 based on the communication with the wireless charger 301. According to an embodiment, the electronic device 101 may control the operating mode of the biometric sensor 276 to be changed to a first operating mode or a second operating mode based on communication with the wireless charger 301. The first operating mode and the second operating mode are exemplary, and the biometric sensor 276 may operate in another operating mode (e.g., an idle mode) in addition to the first operating mode and the second operating mode.

According to an embodiment, as described above with respect to FIG. 2, in the first operating mode, the biometric sensor 276 may be configured to obtain biometric information of an external object (e.g., a user). According to an embodiment, in the second operating mode, the biometric sensor 276 may be configured to perform optical communication with the wireless charger 301 using a light emitting unit (e.g., the light emitting unit 220 in FIG. 2) and the light receiving unit 230. For example, the biometric sensor 276 may include at least one LED for sensing biometric information and at least one LED for optical communication. For example, the LED for optical communication may not be used to detect biometric information.

According to various embodiments, the electronic device 101 may control the operating mode of the biometric sensor 276 based on a request for biometric information. According to an embodiment, when a user input to request for obtaining biometric information is received, the electronic device 101 may control the biometric sensor 276 to be in a first operating mode.

According to various embodiments, the electronic device 101 may control the operating mode of the biometric sensor 276 based on a wireless power signal from the wireless charger 301. According to an embodiment, when a specified wireless power signal (a wireless power signal having the specified band, specified strength, specified period, and/or specified length) is received using the power receiving circuit 210, the processor 120 may control the biometric sensor 276 to be in a second operating mode. For example, when the electronic device 101 and the wireless electronic device 301 are located within a specified distance, a wireless power signal having a specified strength may be received. The strength of the wireless power signal may be described based on the distance between the electronic device 101 and the wireless charger 301.

According to an embodiment, when the specified wireless power signal is received, the power receiving circuit 210 may transmit a control signal to the processor 120. When a control signal is received, the processor 120 may control the biometric sensor 276 to be in the second operating mode. According to an embodiment, when the specified wireless power signal is received, the power receiving circuit 210 may control the biometric sensor 276 to be in the second operating mode by transmitting a control signal (e.g., an interrupt signal) to the biometric sensor 276 through the interface 275.

According to various embodiments, the electronic device 101 may control the operating mode of the biometric sensor 276 based on wireless charging. According to an embodiment, when the wireless charging is started (e.g., enters a wireless charging mode), the electronic device 101 may control the biometric sensor 276 to be in the second operating mode. For example, when the wireless charging is started, the processor 120 may control the biometric sensor 276 to be in the second operating mode. According to an embodiment, when the wireless charging is started, the power receiving circuit 210 may change the operating mode of the biometric sensor 276 to a second operating mode by transmitting a control signal to the biometric sensor 276. According to an embodiment, when a specified wireless power signal is received using the power receiving circuit 210, the electronic device 101 may determine to enter the wireless charging mode.

According to various embodiments, when the wireless charging is terminated, the electronic device 101 may switch the operating mode of the biometric sensor 276 from the second operating mode to the first operating mode. According to an embodiment, when a wireless power signal with a specified magnitude or more is not received during a specified time or longer, the processor 120 or the power receiving circuit 210 may determine that the wireless charging is ended. For example, when it is determined that the wireless charging is ended, the processor 120 may control the biometric sensor 276 in the first operating mode by transmitting a control signal to the biometric sensor 276 through the interface 275. For example, when an interrupt signal or reset signal is received through the interface 275 in the second operating mode, the biometric sensor 276 may operate in the first operating mode.

According to various embodiments, the voltage supplied to the biometric sensor 276 may be different depending on the operating mode. According to an embodiment, in the first operating mode, the power management module 188 may supply the first voltage to the biometric sensor 276. In the second operating mode, the power management module 188 may supply a second voltage different from the first voltage to the biometric sensor 276. For example, the second voltage may be a voltage not greater than the first voltage. According to an embodiment, the first voltage and/or second voltage may be generated from the output voltage of the battery 189, using a converter (e.g., a DC converter). According to an embodiment, the first voltage and/or second voltage may be a voltage obtained by boosting the output voltage of the battery 189 by a booster. According to an embodiment, the second voltage may be a voltage substantially identical to the output voltage of the battery 189. For example, during the wireless charging (e.g., in the second operating mode), a wireless management module 188 may supply the output voltage of the battery 189 to the biometric sensor 276 by bypassing the booster or converter using a switching circuit (not illustrate).

According to various embodiments, the electronic device 101 and the wireless charger 301 may perform optical communication based on the wavelength of light. According to an embodiment, multiple wavelengths of light may indicate different bit values. For example, light of first, second, third, and fourth wavelengths corresponding to wavelengths of different bands may be used for optical communication. The light of the first wavelength may indicate a first value (e.g., 00); the light of the second wavelength may indicate a second value (e.g., 01); the light of the third wavelength may indicate a third value (e.g., 10); and the light of the fourth wavelength may indicate a fourth value (e.g., 11). According to an embodiment, a bit value may be indicated based on the combination of a plurality of light sources of wavelengths. For example, the light of a first wavelength may indicate the first value; the light of a second wavelength may indicate the second value; the light of a third wavelength may indicate the third value; the light of a fourth wavelength may indicate the fourth value; the light of the first and second wavelengths may indicate a fifth value; the light of the first and third wavelengths may indicate a sixth value. For convenience of description, only some combinations of a plurality of wavelengths have been illustrated. However, the optical communication based on the wavelength of light in various embodiments of the specification is not limited thereto. According to various embodiments, the electronic device 101 and the wireless charger 301 may perform optical communication based on the wavelength of light and the strength of light. According to an embodiment, the bit position may be specified based on the wavelength of light. For example, light of first, second, third, and fourth wavelengths corresponding to wavelengths of different bands may be used for optical communication. For example, the light of the first wavelength may indicate the value of the first digit; the light of the second wavelength may indicate the value of the second digit; the light of the third wavelength may indicate the value of the third digit; and the light of the fourth wavelength may indicate the value of the fourth digit. According to an embodiment, the value of each position may be indicated based on the strength of the light. For example, the light with the first strength or higher may indicate a value of "1"; the light with strength less than the first strength may indicate a value of "0". For example, a plurality of strength sections are set depending on the strength of the light, and strength sections may correspond to different values, respectively. According to an embodiment, light with a wavelength corresponding to an ultraviolet ray may indicate the first bit (least significant bit); light with a wavelength corresponding to green may indicate the second bit; light with a wavelength corresponding to blue may indicate the third bit; and light with a wavelength corresponding to red may indicate the fourth bit (e.g., the most significant bit). For example, the light with the first strength or higher may indicate "1"; the light with strength less than the second strength may indicate "0". For example, when only the green LED of the light emitting unit 220 is turned on, the wireless charger 301 may recognize the value of "0010" using the light receiving unit 332.

According to an embodiment, the light of one wavelength may express a plurality of values based on strength. For example, the light of one wavelength may indicate a plurality of bits based on strength. For example, a value of 2 bits may be indicated based on the strength of light of one wavelength. For example, when the strength of light with one wavelength is less than the first strength, it may mean '00'; when the strength of light is greater than the first strength and less than the second strength, it may mean '01'; when the strength of light is greater than the second strength and less than the third strength, it may mean '10'; and when the strength of light with one wavelength is greater than the third strength, it may mean '11'. For example, when each light indicates 2 bits, a value between "00000000" and "11111111" may be simultaneously transmitted through optical communication, using the light (e.g., red, blue, green, and infrared) of four wavelengths.

According to various embodiments, the electronic device 101 and the wireless charger 301 may perform optical communication in an asynchronous scheme. According to an embodiment, when wireless charging is started (e.g., when the biometric sensor 276 is set to the second operating mode), the electronic device 101 may receive an optical signal having a value corresponding to the start of optical communication, using the light receiving unit 230 of the biometric sensor 276. For example, after starting wireless charging, the electronic device 101 may monitor the light signal using the light receiving unit 230. When wireless charging starts, the wireless charger 301 may transmit a light signal having a value (e.g., a start bit) corresponding to the start of optical communication, using the light emitting unit 331. According to an embodiment, when the wireless charging is started, the electronic device 101 may transmit a light signal having a value corresponding to the start of optical communication, using the light emitting unit 220 of the biometric sensor. For example, after starting wireless charging, the wireless charger 301 may monitor the light signal using the light receiving unit 332. When wireless charging starts, the wireless charger 301 may receive a light signal having a value (e.g., a start bit) corresponding to the start of optical communication, using the light receiving unit 332. For example, after transmission or reception of the start bit, the electronic device 101 and the wireless charger 301 may perform data communication using optical communication. According to an embodiment, the electronic device 101 or the wireless charger 301 may indicate the end of data communication or the end of a data block by transmitting a value (e.g., an end bit) indicating the end of optical communication.

According to an embodiment, the electronic device 101 and the wireless charger 301 may perform asynchronous optical communication based on a specified sampling rate. For example, in the first operating mode, the biometric sensor 276 may operate at a first sampling rate; in the second operating mode, the biometric sensor 276 may operate at a second sampling rate different from the first sampling rate. For example, similarly to universal asynchronous receiver/transmitter (UART) communication, the biometric sensor 276 in the second operating mode may perform sampling with a clock 16 or 64 times higher than the biometric sensor 276 in the first operating mode.

According to various embodiments, the transmission from the electronic device 101 to the wireless charger 301 may be performed based on optical communication using the biometric sensor 276; the transmission from the wireless charger 301 to the electronic device 101 may be performed based on a wireless power signal using the power transmitting circuit 310. For example, the optical signal transceiver 330 may not include the light emitting unit 331. For example, a logical high and low may be indicated based on the magnitude and/or time of the wireless power signal. For example, when the wireless power signal of the specified magnitude or more is continued during a specified time or longer, the electronic device 201 may recognize the wireless power signal as a logical high.

Figure 4:
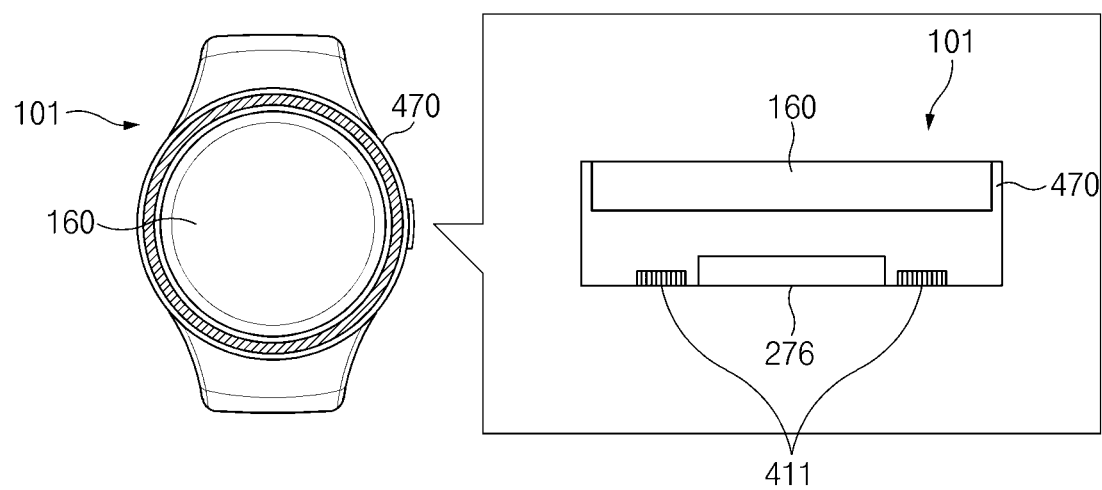
FIG. 4 illustrates a schematic diagram of an electronic device according to various embodiments.

FIG. 4 illustrates a schematic diagram 400 of the electronic device 101 according to various embodiments.

According to various embodiments, the electronic device 101 may be a wearable device (e.g., a smart watch). According to an embodiment, the electronic device 101 may include the display device 160 positioned on the front side of housing 470. For example, the display device 160 may include a display capable of receiving a touch input. According to an embodiment, the electronic device 101 may include the biometric sensor 276 positioned on the rear side of the housing 470. According to an embodiment, the electronic device 101 may include a reception coil 411 positioned around the biometric sensor 276. For example, the reception coil 411 may be a part of the power receiving circuit 210 of FIG. 2. For example, the reception coil 411 may be positioned to surround the biometric sensor 276. According to an embodiment, the reception coil 411 may have the specified number of windings and may be configured to receive a signal from an external electronic device (e.g., the wireless charger 301 in FIG. 3).

Figure 5:
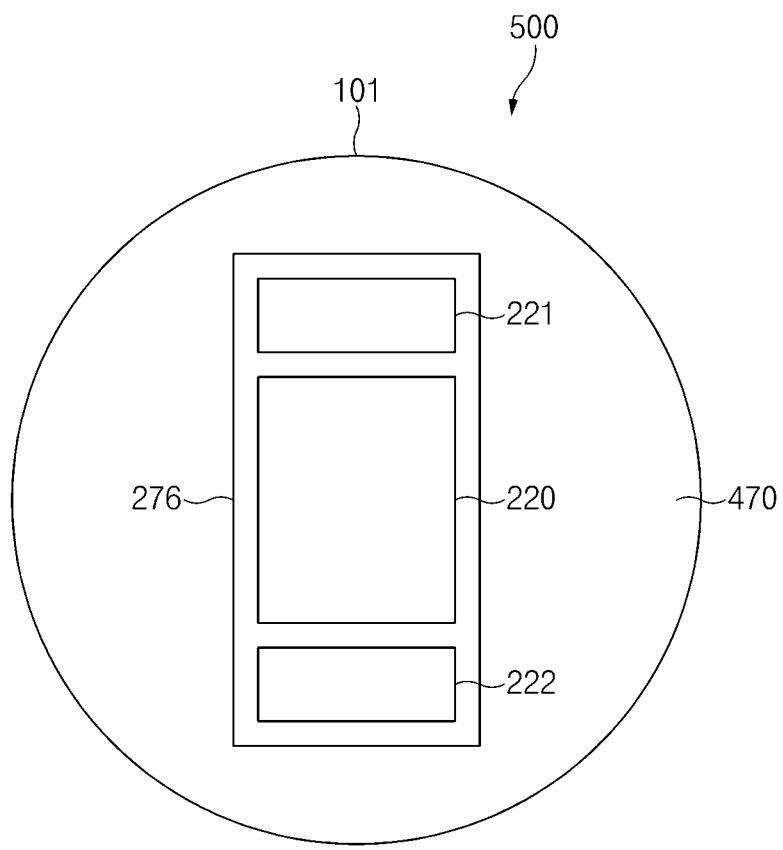
FIG. 5 illustrates a schematic diagram of a biometric sensor according to various embodiments.

FIG. 5 illustrates a schematic diagram 500 of the biometric sensor 276 according to various embodiments.

According to various embodiments, the biometric sensor 276 may be disposed on the rear side of the housing 470, and thus the biometric sensor 276 may face a user's skin at point in time when the electronic device 101 is worn by the user. According to an embodiment, the biometric sensor 276 may include a first light emitting unit 221, a second light emitting unit 222, and the light receiving unit 230. For example, the first light emitting unit 221 and the second light emitting unit 222 may correspond to at least one of a plurality of LEDs included in the light emitting unit 220 of FIG. 2. The first light emitting unit 221 and the second light emitting unit 222 may provide light having different wavelengths from each other. For example, the first light emitting unit 221 may provide light corresponding to a plurality of wavelengths. For example, the second light emitting unit 222 may provide light corresponding to a plurality of wavelengths. For example, the light receiving unit 230 may include at least one photodiode.

Figure 6:
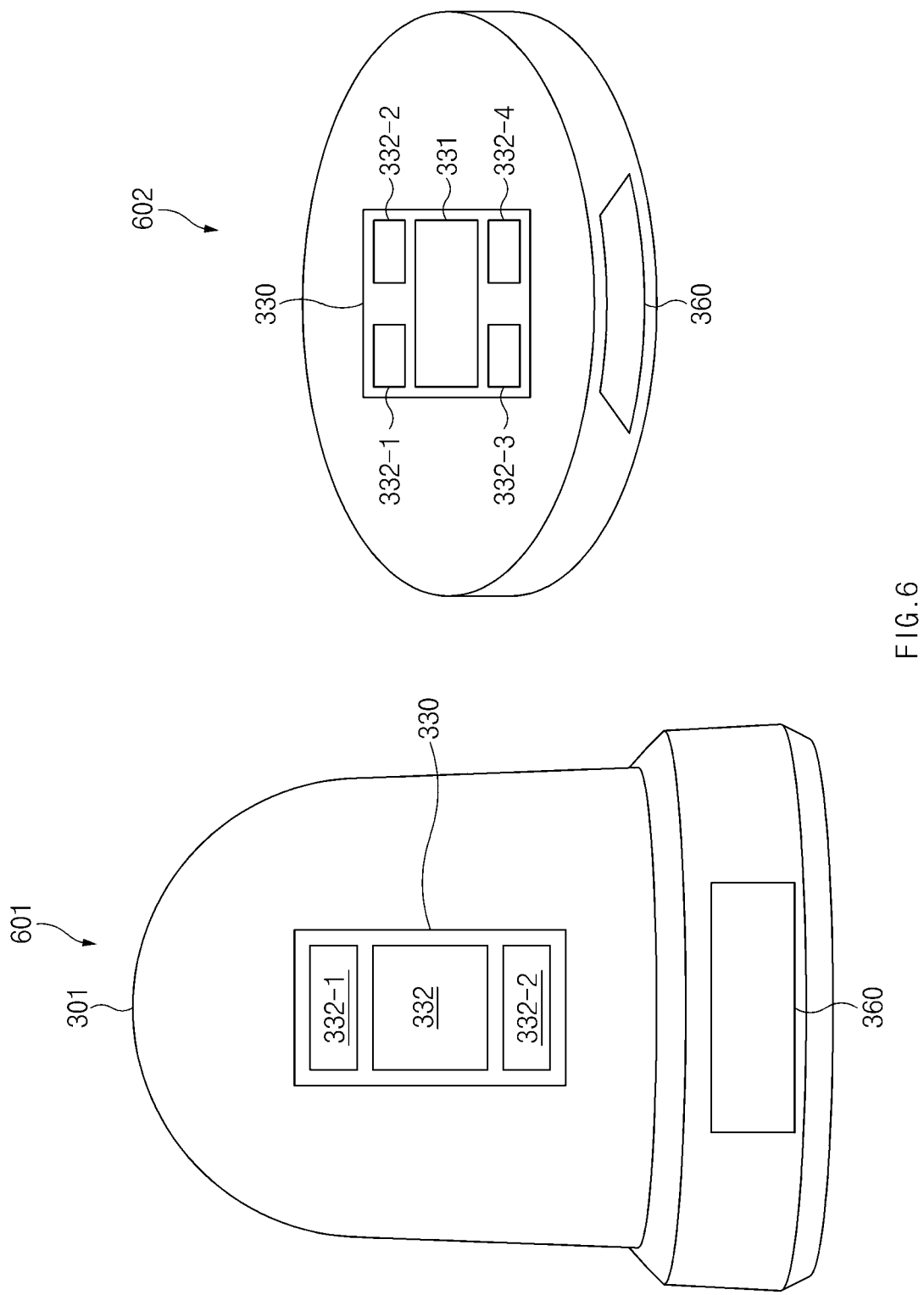
FIG. 6 illustrates schematic diagrams of a wireless charger according to various embodiments.

FIG. 6 illustrates schematic diagrams of the wireless charger 301 according to various embodiments.

According to various embodiments, the wireless charger 301 may include the optical signal transceiver 330 positioned on at least one side of the wireless charger 301. For example, the optical signal transceiver 330 may be positioned on a side adjacent to the rear side of the electronic device 101 when the electronic device 101 is positioned.

Referring to reference number 601, according to various embodiments, the optical signal transceiver 330 may include a first light receiving unit 332-1, a second light receiving unit 332-2, and the light emitting unit 331. For example, the light emitting unit 331 may include at least one LED. A plurality of LEDs of the light emitting unit 331 may be configured to emit light having different wavelengths from each other. For example, each of the first light receiving unit 332-1 and the second light receiving unit 332-2 may include at least one photodetector (e.g., a photodiode). Referring to reference number 602, according to various embodiments, the optical signal transceiver 330 may include the first light receiving unit 332-1, the second light receiving unit 332-2, a third light receiving unit 333-3, a fourth light receiving unit 334-4, and the light emitting unit 331. For example, the light emitting unit 331 may include at least one LED. A plurality of LEDs of the light emitting unit 331 may be configured to emit light having different wavelengths from each other. For example, the light receiving units 332-1, 332-2, 332-3, and 332-4 may include at least one photodetector (e.g., a photodiode).

The placement of the display 360 and the optical signal transceiver 330 illustrated in reference numerals 601 and 602 is exemplary. The shape of the wireless charger 301 of the disclosure is not limited thereto.

Figure 7:
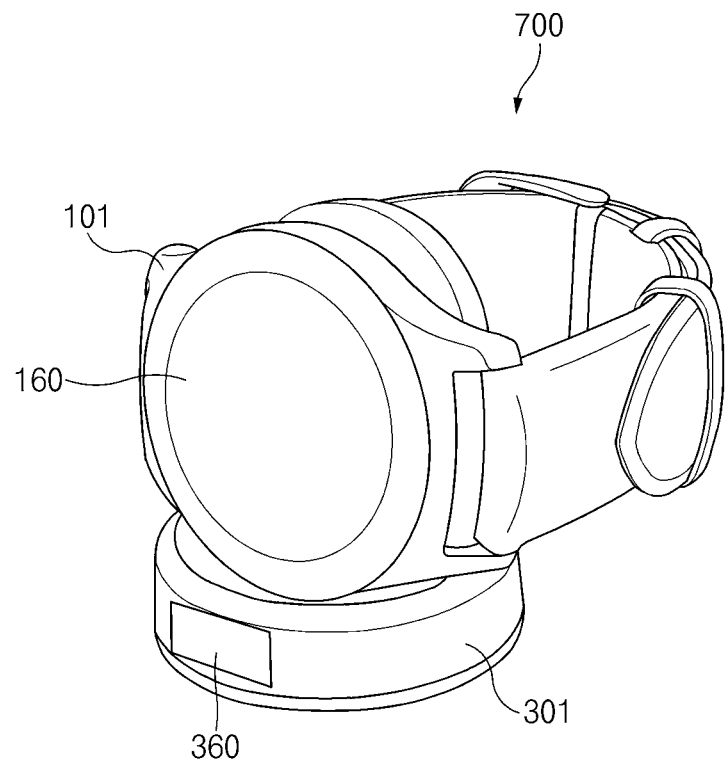
FIG. 7 illustrates a charging situation according to various embodiments.

FIG. 7 illustrates a charging situation 700 according to various embodiments.

According to various embodiments, the electronic device 101 may be mounted on the wireless charger 301. For example, the electronic device 101 may be positioned within a distance capable of performing wireless charging based on a wireless power signal from the wireless charger 301. For example, the electronic device 101 may perform wireless charging by being mounted at a specified location of the wireless charger 301. When the electronic device 101 is mounted incorrectly, the electronic device 101 may fail to perform wireless charging. For example, when the electronic device 101 is tilted, the electronic device 101 may fail to perform fast charging. According to an embodiment, the electronic device 101 may control wireless charging based on communication with the wireless charger 301.

Figure 8:
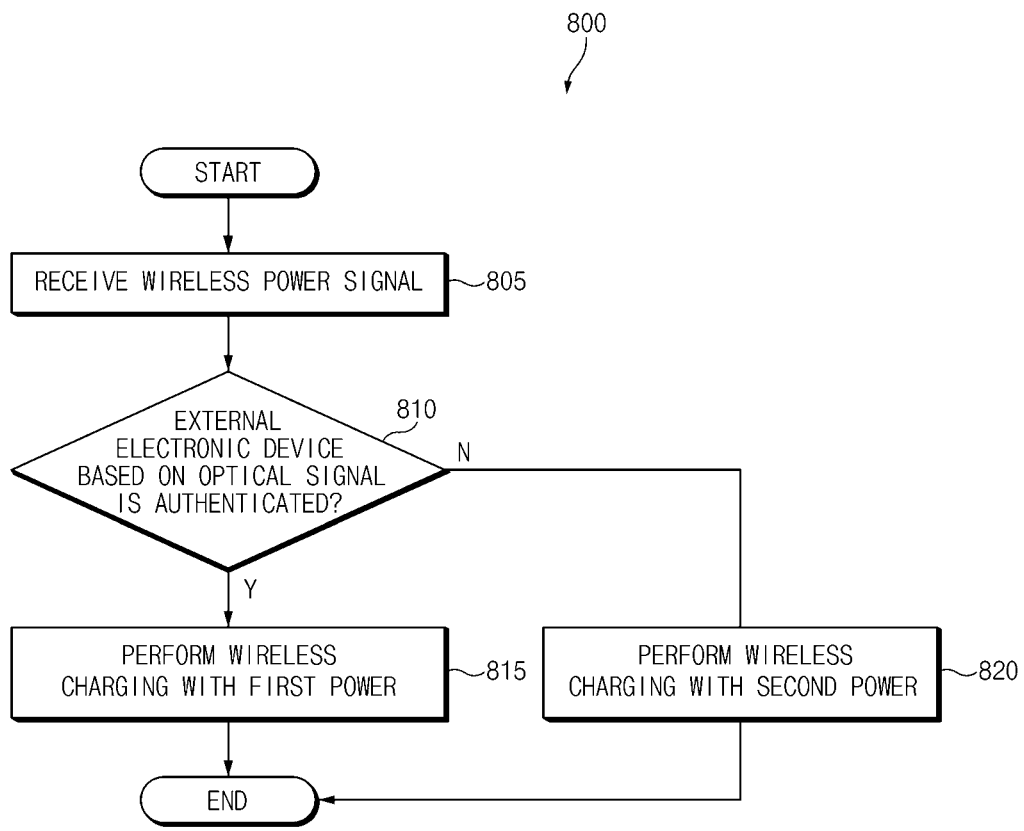
FIG. 8 is a flowchart of a wireless charging control method according to an embodiment.

FIG. 8 is a flowchart of a wireless charging control method 800 according to an embodiment.

According to various embodiments, in operation 805, an electronic device (e.g., the electronic device 101 of FIG. 2) may receive a wireless power signal from an external electronic device (e.g., the wireless charger 301 of FIG. 3). For example, the electronic device 101 may receive a wireless power signal using the power receiving circuit 210. For example, the wireless power signal may be a wireless power signal having a specified time and/or a specified time interval. According to an embodiment, the wireless power signal may be a signal indicating the start of wireless charging. For example, as described above, when the wireless power signal is received, the electronic device 101 may control an operating mode of the biometric sensor 276 as a second operating mode.

According to various embodiments, in operation 810, the electronic device 101 may authenticate the external electronic device based on an optical signal. According to an embodiment, when the specified optical signal (the light signal with a specified wavelength and/or specified amount of light) is received by the biometric sensor 276, the electronic device 101 may determine that the external electronic device is authenticated. For example, when the specified optical signal is received within the specified time, the electronic device 101 may determine that the external electronic device is authenticated.

According to various embodiments, when the external electronic device is authenticated, in operation 815, the electronic device 101 may perform wireless charging with the first power. For example, when the external electronic device is authenticated, the electronic device 101 may charge the battery 189 with the first power, using the wireless power signal from the external electronic device.

According to various embodiments, when the external electronic device is not authenticated, in operation 820, the electronic device 101 may perform wireless charging with the second power. For example, the electronic device 101 may charge the battery 189 with the second power, using the wireless power signal from the external electronic device.

According to an embodiment, the first power may be power corresponding to fast charging; the second power may be power corresponding to normal charging. For example, when the wireless charging is performed with the first power, the electronic device 101 may display information indicating fast charging on a display (e.g., the display device 160 of FIG. 1).

According to various embodiments, in operation 805, an electronic device (e.g., the electronic device 101 of FIG. 2) may receive a wireless power signal from an external electronic device (e.g., the wireless charger 301 of FIG. 3). For example, the electronic device 101 may receive a wireless power signal using the power receiving circuit 210. For example, the wireless power signal may be a wireless power signal having a specified time and/or a specified time interval. According to an embodiment, the wireless power signal may be a signal indicating the start of wireless charging. According to an embodiment, when receiving a wireless charging power signal, configuration information of an external electronic device (e.g., the wireless charger 301 of FIG. 3) may be received, and the wireless power may be received from the external electronic device based on the configuration information. For example, the electronic device 101 may perform wireless charging with the first or second power based on the configuration information. In this case, operation 810, operation 815, and operation 820 may be omitted.

Figure 9:
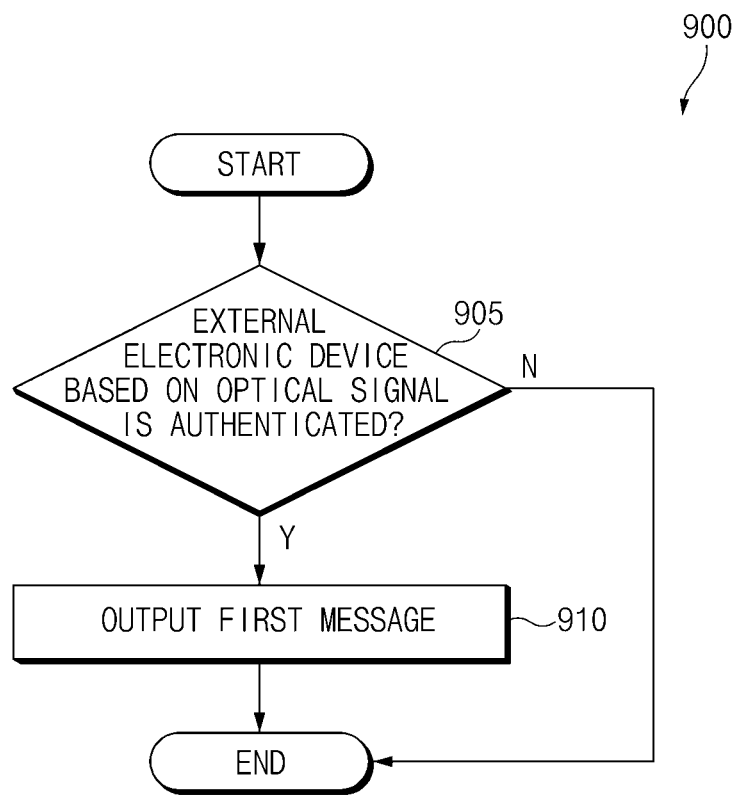
FIG. 9 is a flowchart of a wireless charging control method according to an embodiment.

FIG. 9 is a flowchart of a wireless charging control method 900 according to an embodiment.

For example, the wireless charging control method 900 of FIG. 9 may be performed after operation 805 of FIG. 8.

According to various embodiments, in operation 905, the electronic device 101 may output a first message. According to an embodiment, the electronic device 101 may output information indicating that the external electronic device (e.g., a wireless charger) is not a dedicated charger, as the first message. According to an embodiment, the electronic device 101 may output a message indicating adjusting locations of the electronic device 101 and the external electronic device, as the first message. According to an embodiment, the electronic device 101 may visually and/or audibly output the first message.

According to various embodiments, in operation 905, the electronic device 101 may authenticate an external electronic device (e.g., the wireless charger 301 of FIG. 3) based on an optical signal. According to an embodiment, when the specified optical signal (the light signal with a specified wavelength and/or specified amount of light) is received by the biometric sensor 276, the electronic device 101 may determine that the external electronic device is authenticated. For example, when the specified optical signal is received within the specified time, the electronic device 101 may determine that the external electronic device is authenticated.

According to various embodiments, when the external electronic device (e.g., the wireless charger 301 in FIG. 3) is authenticated, in operation 910, the electronic device 101 may output the first message. According to an embodiment, the electronic device 101 may output the first message, using the display 360 of the wireless charger 301. For example, the electronic device 101 may transmit the first message or data including the first message to the wireless charger 301 based on optical communication using the biometric sensor 276. For example, when the first message is received, the wireless charger 301 may display the first message on the display 360. For example, the wireless charger 301 may output the first message using an audio output device (not illustrated). For example, the first message may include information (e.g., a notification associated with the electronic device 101, information about status of charging, message arrival, mail arrival, and/or receiving a call) associated with the electronic device 101. According to an embodiment, the first message may include information about the theme (e.g., a background, icon theme, and/or accessory (e.g., housing or strap)) of the electronic device 101. For example, the wireless charger 301 may display an image corresponding to information included in the first message on the display 360. For example, a thematic unification may be provided by outputting an image corresponding to the background set in the electronic device 101 to the display 360. According to an embodiment, the first message may include an image or information associated with the theme of the electronic device 101. For example, the wireless charger 301 may output an image or information included in the first message.

According to an embodiment, when the authentication of the external electronic device fails, the electronic device 101 may output a second message. For example, the electronic device 101 may output the second message, using the display device 160 and/or the sound output device 155 of the electronic device 101. For example, the second message may include information about unstable coupling between the electronic device 101 and an external electronic device (e.g., the wireless charger 301). The second message may include information indicating that the electronic device 101 is tilted or is not properly coupled with the external electronic device. For example, the second message may include information for guiding changing the mounting state of the electronic device 101. For example, the second message may include information indicating that optical communication between the electronic device 101 and the external electronic device is impossible.

According to various embodiments, after operation 905, the electronic device 101 may attempt to authenticate the external electronic device again. For example, the electronic device 101 may attempt to authenticate the external electronic device at a specified cycle. For example, the electronic device 101 may attempt to authenticate the external electronic device within the specified number or during a specified period. When the authentication of the external electronic device fails within the specified number or during the specified period, the electronic device 101 may not authenticate the external electronic device anymore. For example, the electronic device 101 may change the operating mode of the biometric sensor 276 to a first operating mode again.

Figure 10:
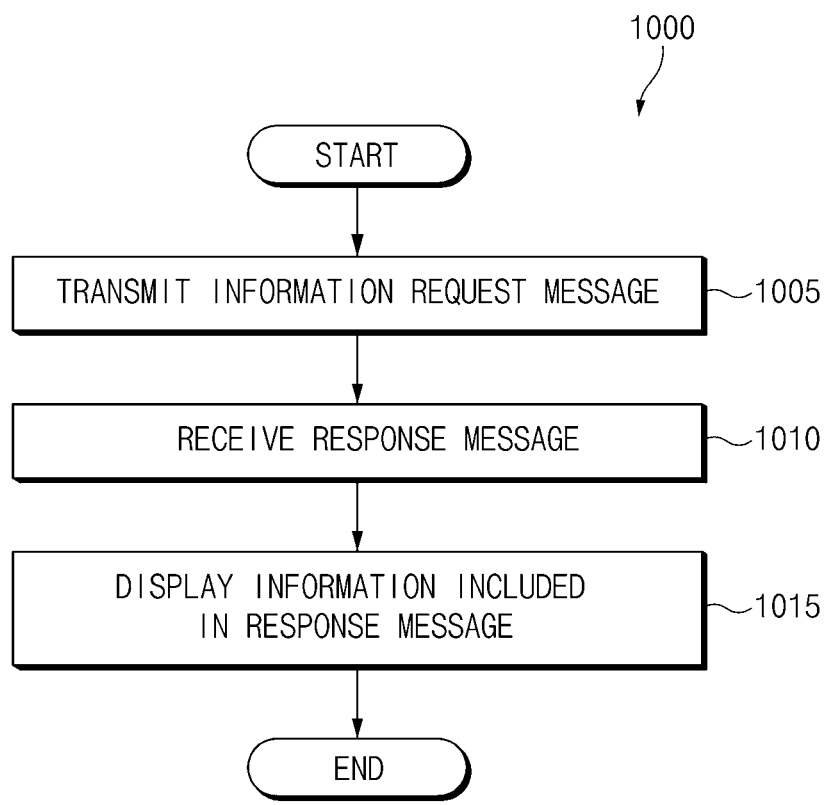
FIG. 10 is a flowchart of a method for displaying information according to various embodiments.

FIG. 10 is a flowchart of a method 1000 for displaying information according to various embodiments.

According to various embodiments, in operation 1005, a wireless charger (e.g., the wireless charger 301 of FIG. 3) may transmit an information request message to the electronic device 101. For example, the wireless charger 301 may transmit the information request message to the electronic device 101, using the optical signal transceiver 330. For example, the wireless charger 301 may transmit the information request message to the electronic device 101, using the power transmitting circuit 310.

According to various embodiments, in operation 1010, the wireless charger 301 may receive a response message from the electronic device 101. According to an embodiment, the wireless charger 301 may receive the response message, using the optical signal transceiver 330.

According to various embodiments, in operation 1015, the wireless charger 301 may display information included in the response message, using the display 360. According to an embodiment, the information may include the status of charging of the electronic device 101. According to an embodiment, the information may include the model name of the electronic device 101. According to an embodiment, the information may be a notification (e.g., an incoming message, incoming call, and/or recipient information) associated with the electronic device 101.

According to various embodiments, operation 1005 may be omitted. For example, the wireless charger 301 may be configured to receive a message from the electronic device 101 and to display information included in the message on the display 360.

Figure 11:
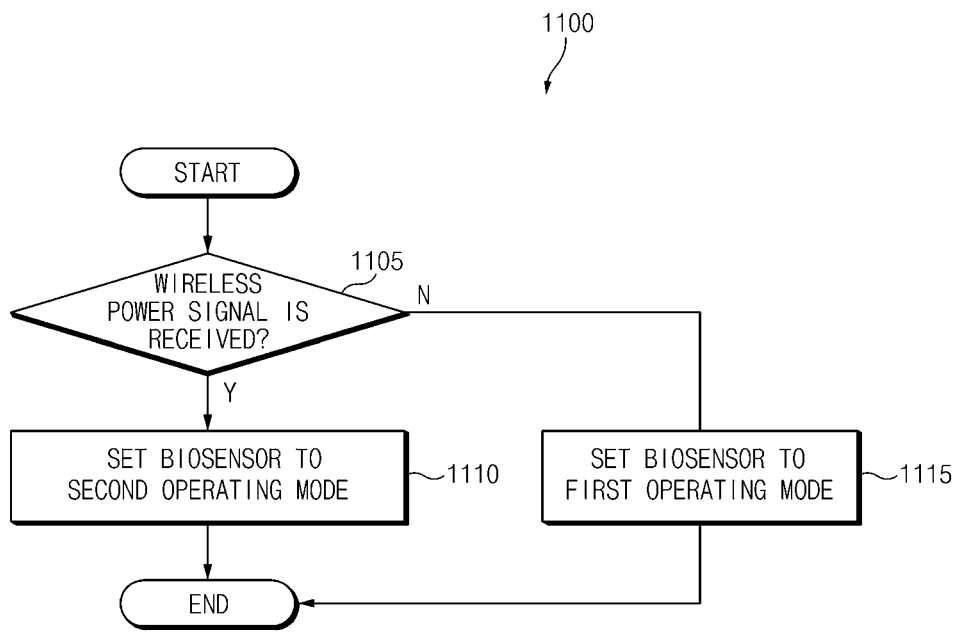
FIG. 11 is a flowchart of a method for controlling an electronic device according to various embodiments.

FIG. 11 is a flowchart of a method 1100 for controlling the electronic device 101 according to various embodiments.

According to various embodiments, in operation 1105, an electronic device (e.g., the electronic device 101 of FIG. 2) may determine whether a wireless power signal is received from an external electronic device (e.g., the wireless charger 301 of FIG. 3). For example, the electronic device 101 may receive a wireless power signal using the power receiving circuit 210. For example, the wireless power signal may be a wireless power signal having a specified time and/or a specified time interval. According to an embodiment, the wireless power signal may be a signal indicating the start of wireless charging.

According to various embodiments, when the wireless power signal is received, in operation 1110, the electronic device 101 may set the biometric sensor 276 to a second operating mode. According to an embodiment, in the second operating mode, the electronic device 101 may perform optical communication with the external electronic device (e.g., the wireless charger 301 of FIG. 3), using the biometric sensor 276. For example, the biometric sensor may include at least one LED (e.g., the light emitting unit 220 of FIG. 2)

and at least one light receiving unit (e.g., the light receiving unit 230 of FIG. 2). The at least one LED includes a first LED and a second LED; and the first LED and the second LED may be configured to output light having different wavelengths from each other.

According to an embodiment, the electronic device 101 may output light using the at least one LED, may detect light from the external electronic device using the at least one light receiving unit, and may perform optical communication with the external electronic device based on the detected light.

According to an embodiment, after the specified wireless power signal is received, when a specified optical signal is received from the external electronic device using the biometric sensor 276, the electronic device 101 may charge the battery 189 of the electronic device 101 with the first power, using the wireless power signal received from the external electronic device. After the specified wireless power signal is received, when the specified optical signal is not received from the external electronic device using the biometric sensor 276, the electronic device 101 may charge the battery 189 with the second power, using the wireless power signal received from the external electronic device. For example, the first power may have a higher value than the second power.

According to an embodiment, in the second operating mode, the electronic device 101 may transmit information associated with the electronic device 101 to the external electronic device, using the biometric sensor 276. For example, the information associated with the electronic device 101 may include at least one of the status of charging of the electronic device 101, the notification of the electronic device 101, or the model name of the electronic device 101.

According to various embodiments, in operation 1115, when the wireless power signal is not received, the electronic device 101 may set the biometric sensor 276 to a first operating mode. According to an embodiment, in the first operating mode, the electronic device 101 may obtain biometric information, using the biometric sensor 276. According to an embodiment, in the first operating mode, when a request is received to obtain the biometric information, the electronic device 101 may irradiate light having at least one of a specified wavelength or a specified strength, using at least one LED, may obtain the light obtained as the irradiated light is reflected by the external object, using the at least one light receiving unit, and may obtain the biometric information based on the obtained light.

Returning to FIG. 2, according to various embodiments, the electronic device 101 may include the biometric sensor 276 including at least one light emitting diode (LED) (e.g., the light emitting unit 220) and at least one light receiving unit (e.g., the light receiving unit 230) and obtaining biometric information using the at least one LED and the at least one light receiving unit, the power receiving circuit 210 receiving a wireless power signal from an external electronic device (e.g., the wireless charger 301 of FIG. 3), and the processor 120 operatively coupled to the biometric sensor 276 and the power receiving circuit 210. According to an embodiment, the processor 120 may be configured to receive a specified wireless power signal from the external electronic device 301, using the power receiving circuit 210, and to perform optical communication with the external electronic device 301, using the biometric sensor 276 when receiving the specified wireless power signal.

According to an embodiment, the processor 120 may be configured to output light using the at least one LED 220, to detect light from the external electronic device 301, using the at least one light receiving unit 230, and to perform the optical communication with the external electronic device 301 based at least on the detected light from the external electronic device 301.

According to an embodiment, the processor 120 may be configured to output light of a specified wavelength or specified strength, using the at least one LED 220.

According to an embodiment, the at least one LED 220 may include a first LED and a second LED. The first LED and the second LED may be configured to output light of different wavelengths from each other.

According to an embodiment, the electronic device 101 may further include the battery 189. The processor 120 may be configured to charge the battery with a first power, using the wireless power signal received from the external electronic device 301 after the specified wireless power signal is received, when receiving a specified optical signal from the external electronic device 301 by using the biometric sensor 276. The processor 120 may be configured to charge the battery with a second power, using the wireless power signal received from the external electronic device 301 after the specified wireless power signal is received, when not receiving a specified optical signal from the external electronic device 301 by using the biometric sensor 276. For example, the first power may be higher than the second power.

According to an embodiment, the processor 120 may be configured to control the biometric sensor 276 to be in a first operating mode when not receiving the specified wireless power signal, and to control the biometric sensor 276 to be in a second operating mode when receiving the specified wireless power signal. The biometric sensor 276 may be configured to obtain biometric information in the first operating mode. The biometric sensor 276 may be configured to perform the optical communication with the external electronic device in the second operating mode.

According to an embodiment, the processor 120 may transmit information associated with the electronic device 101 to the external electronic device 301, using the biometric sensor 276 in the second operating mode. For example, the information associated with the electronic device may include at least one of a status of charging of the electronic device, a notification of the electronic device, or a model name of the electronic device.

According to an embodiment, in the second operating mode, the processor 120 may be configured to irradiate light of a specified wavelength or specified strength, using the at least one LED 220, to obtain light obtained as the irradiated light is reflected by an external object, using the at least one light receiving unit 230, and to obtain the biometric information based at least on the obtained reflected light.

According to various embodiments, the electronic device 101 may include a light emitting unit 220 outputting light, at least one light receiving unit 230, a power receiving circuit 210, and a processor 120. According to an embodiment, the processor 120 the processor 120 may be configured to receive a request for obtaining a biometric signal corresponding to a living body, and to obtain at least part of light reflected by the living body among the light output through the light emitting unit 220, using the light receiving unit 230 and then detect the biometric signal based at least partly on the obtained light when receiving the request. According to an embodiment, the processor 120 may be configured to communicate with the external electronic device 301, using the light receiving unit 230 and the light emitting unit 220 when being coupled to an external electronic device 301 using the power receiving circuit 210.

According to an embodiment, the light emitting unit 220 may include at least one first LED for outputting first light having a first wavelength, and at least one second LED for outputting second light having a second wavelength.

According to an embodiment, the processor 120 may be configured to adjust at least one of a wavelength or strength of light output using the LED 220 and to control data to be transmitted to the external electronic device 301 based at least on light obtained as the wavelength or the strength of the light is adjusted.

According to an embodiment, the electronic device 101 may further include the battery 189. The processor 120 may charge the battery 189 to be in a first state or a second state based on the communication with the external electronic device 301 using the light receiving unit 230 and the light emitting unit 220. For example, a first charging power in the first state may be higher than a second charging power in the second state.

According to an embodiment, the electronic device 101 may further include a display (e.g., the display device 160). The processor may be configured to display information associated with charging in the second state, using the display while charging the battery 189 to be in the second state.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

The invention claimed is:

1. An electronic device comprising:
   a biometric sensor including at least one light emitting diode (LED) and at least one light receiving unit and configured to obtain biometric information using the at least one LED and the at least one light receiving unit;
   a battery;
   a power receiving circuit configured to receive a wireless power signal from a wireless charging device; and
   a processor operatively coupled to the biometric sensor and the power receiving circuit, wherein the processor is configured to:
control the biometric sensor to obtain the biometric information;
receive a specified wireless power signal from the wireless charging device, using the power receiving circuit;
in response to receiving the specified wireless power signal, control the biometric sensor to perform optical communication;
after receiving the specified wireless power signal, when a specified optical signal from the wireless charging device is received by using the biometric sensor, determine that the wireless charging device is authenticated based on the specified optical signal from the optical communication with the wireless charging device, using the biometric sensor;
when the wireless charging device is authenticated, perform wireless charging of the battery with a first power; and
when the wireless charging device not authenticated, perform wireless charging of the battery with a second power,
wherein the second power corresponds to a normal charging, and
wherein the first power corresponds to a charging faster than the normal charging.

2. The electronic device of claim 1, wherein the processor is configured to:
output light using the at least one LED;
detect light from the wireless charging device, using the at least one light receiving unit; and
perform the optical communication with the wireless charging device based at least on the detected light from the wireless charging device.

3. The electronic device of claim 2, wherein the processor is configured to:
output light of a specified wavelength or specified strength, using the at least one LED.

4. The electronic device of claim 1, wherein the at least one LED includes a first LED and a second LED, and
wherein the first LED and the second LED are configured to output light of different wavelengths from each other.

5. The electronic device of claim 1, wherein the processor is configured to:
when not receiving the specified wireless power signal, control the biometric sensor to be in a first operating mode; and
when receiving the specified wireless power signal, control the biometric sensor to be in a second operating mode,
wherein the biometric sensor is configured to obtain the biometric information in the first operating mode, and
wherein the biometric sensor is configured to perform the optical communication with the wireless charging device in the second operating mode.

6. The electronic device of claim 5, wherein the processor transmits information associated with the electronic device to the wireless charging device, using the biometric sensor in the second operating mode, and
wherein the information associated with the electronic device includes at least one of a status of charging of the electronic device, a notification of the electronic device, or a model name of the electronic device.

7. The electronic device of claim 5, wherein the processor is configured to:
in the second operating mode,
irradiate light of a specified wavelength or specified strength, using the at least one LED;
obtain light obtained as the irradiated light is reflected by an external object, using the at least one light receiving unit; and
obtain the biometric information based at least on the obtained reflected light.

8. An optical communication method of an electronic device, the method comprising:
controlling a biometric sensor of the electronic device to obtain biometric information;
receiving a specified wireless power signal from a wireless charging device, using a power receiving circuit of the electronic device; and
in response to receiving the specified wireless power signal, control the biometric sensor to perform optical communication;
after the specified wireless power signal is received, when a specified optical signal from the wireless charging device is received by using the biometric sensor, determining that the wireless charging device is authenticated based the specified optical signal from the optical communication with the wireless charging device, using the biometric sensor,
when the wireless charging device is authenticated, performing wireless charging of a battery of the electronic device with a first power; and
when the wireless charging device not authenticated, performing wireless charging of the battery with a second power,
wherein the second power corresponds to a normal charging,
wherein the first power corresponds to a charging faster than the normal charging, and
wherein the biometric sensor includes at least one LED and at least one light receiving unit.

9. The method of claim 8, further comprising:
outputting light using the at least one LED;
detecting light from the wireless charging device using the at least one light receiving unit; and
performing optical communication with the wireless charging device based on the detected light.

10. The method of claim 8, wherein the at least one LED includes a first LED and a second LED, and
wherein the first LED and the second LED are configured to output light having different wavelengths from each other.

11. The method of claim 8, further comprising:
when the specified wireless power signal is not received, controlling the biometric sensor to be in a first operating mode for obtaining the biometric information,
wherein the performing of the optical communication with the wireless charging device, using the biometric sensor of the electronic device when the specified wireless power signal is received includes:
controlling the biometric sensor to be in a second operating mode for the optical communication.

12. The method of claim 11, further comprising, in the second operating mode:
transmitting information associated with the electronic device to the wireless charging device, using the biometric sensor,
wherein the information associated with the electronic device includes at least one of a status of charging of the electronic device, a notification of the electronic device, or a model name of the electronic device.

* * * * *